(12) United States Patent
Li et al.

(10) Patent No.: US 6,783,699 B2
(45) Date of Patent: Aug. 31, 2004

(54) EUROPIUM-CONTAINING FLUORESCENT NANOPARTICLES AND METHODS OF MANUFACTURE THEREOF

(75) Inventors: Guangjun Li, Carmel, IN (US); Hong Wu, Golden, CO (US); Chunyang Liu, Beijing (CN)

(73) Assignee: MedGene, Inc., Palo Alto, CA (US)

( * ) Notice: Subject to any disclaimer, the term of this patent is extended or adjusted under 35 U.S.C. 154(b) by 0 days.

(21) Appl. No.: 10/274,253

(22) Filed: Oct. 17, 2002

(65) Prior Publication Data

US 2004/0075083 A1 Apr. 22, 2004

(51) Int. Cl.$^7$ .......................... C09K 11/02; C09K 11/64
(52) U.S. Cl. .............................. 252/301.4 R; 428/403; 428/405
(58) Field of Search ................... 252/301.4 R; 428/405, 428/403

(56) References Cited

U.S. PATENT DOCUMENTS

| | | | | |
|---|---|---|---|---|
| 5,424,006 A | * | 6/1995 | Murayama et al. | ... 252/301.4 R |
| 5,893,999 A | * | 4/1999 | Tamatani et al. | ..... 252/301.4 R |
| 6,010,644 A | | 1/2000 | Fu et al. | |
| 6,180,354 B1 | | 1/2001 | Singh et al. | |
| 6,228,787 B1 | | 5/2001 | Pavel | |
| 6,261,477 B1 | | 7/2001 | Fu et al. | |
| 6,284,156 B1 | | 9/2001 | Uehara et al. | |
| 6,423,247 B1 | * | 7/2002 | Fukushima et al. | ... 252/301.4 R |

OTHER PUBLICATIONS

Anisimova (1996), "Microwave–Assisted Rapid Solid–State Chemistry of Phosphate Materials," *Phosphorus Sulfur and Silicon and the Related Elements* 111(1–4):640 (abstract only).

Bougrin et al. (2000), "Novel Synthesis of 2–trifluoromethylarylimidazoles on Montmorillonite K10 in a 'Dry Medium' Under Microwave Irradiation, " *Tetrahedron* 57(1):163–168 (abstract only).

Bruchez et al. (1998), "Semiconductor Nanocrystals as Fluorescent Biological Labels," *Science* 281:2013–2016.

Chan et al. (1998), "Quantum Dot Bioconjugates for Ultrasensitive Nonisotopic Detection," *Science* 281:2016–2018.

Dandia et al. (1999), "An Efficient Procedure for the Synthesis of Spiro [3H–Indole–3,4 '(1'H) Pyrano [2,3–C]Pyrrole]–5 '–Carbonitriles Using Solid Inorganic Supports and Microwave Activation," *Synthetic Communications* 29(13):2323–2335 (abstract only).

Gupta et al. (1998), "Dry Synthesis of 'Biginelli 'Compounds Using Inorganic Solid Support Coupled with Microwave Irradiation: An Environmentally Co–Friendly Synthesis,"*Indian Journal of Chemical Technology* 5(5):340–342 (abstract only).

Kubrakova (2000), "Effect of Microwave Radiation on Physicochemical Processes in Solutions and Heterogeneous Systems: Applications in Analytical Chemistry," *Journal of Analytical Chemistry* 55(12):1113–1122 (abstract only).

(List continued on next page.)

*Primary Examiner*—C. Melissa Koslow
(74) *Attorney, Agent, or Firm*—Reed & Eberle LLP

(57) ABSTRACT

Europium-containing fluorescent nanoparticles and methods of preparing such nanoparticles are provided. The nanoparticles are comprised of an aluminum oxide framework having a europium activator, a magnesium, calcium, strontium, or barium energy reservoir, and at least one co-activator selected from the group consisting of scandium, yttrium, and certain lanthanide elements. The nanoparticles may be optionally coated with a silane coating containing reactive functional groups that allow for attachment of the nanoparticle to a desired biological or chemical target molecule. The coated nanoparticles may be used to detect a variety of protein ligand interactions, and may also be used in assays for nucleic acids.

17 Claims, 3 Drawing Sheets

OTHER PUBLICATIONS

Kubrakova (2002), "Microwave Radiation in Analytical Chemistry: The Scope and Prospects for Application," *Uspekhi Khimii* 71(4):327–340 (abstract only).

Lio et al. (2002), A Novel Way to Prepare n–Butylparaben Under Microwave Irradiation, *Tetrahedron Letters* 43(1):45–48 (abstract only).

Murugan et al. (1995), "Microwave–Solvothermal Synthesis of Nanocrystalline Cadmium Sulfide," Materials Chemistry and Physics 71(1):98–102 (abstract only).

Service (1998), "Semiconductor Beacons Light Up Cell Structures," *Science* 281:1930–1931.

Suarez et al. (1996), "An Efficient Procedure to Obtain Hexahydroquinoleines and Unsymmetrical 1,4–Dihydropyridines Using Solid Inorganic Supports and Microwave Activation," *Hetrocyclic Communications* 2(3):275–280 (abstract only).

Tsai et al. (1997), "Aligned Aluminophosphate Molecular Sieves Crystallized on Floating Anodized Alujina by Hydrothermal Microwave Heating," *Advanced Materials* 9(15);1154 (abstract only).

Wada et al. (2001), "Microwave–Assisted Size Control of CdS Nanocrystallites," *Journal of Materials Chemistry* 11(7):1936–1940 (abstract only).

Wang et al. (2002), "The Research Progress in the Preparation of Nanosized Particles by Microwave Dielectric Heating Method of Liquid Phase," Chinese Journal of Inorganic Chemistry 18(4):329–334 (abstract only).

* cited by examiner

EUROPIUM-CONTAINING FLUORESCENT NANOPARTICLES AND METHODS OF MANUFACTURE THEREOF

TECHNICAL FIELD

The present invention relates generally to luminescent nanoparticles and methods for their preparation.

BACKGROUND OF THE INVENTION

Fluorescence is the emission of light by a material when the material is excited by an external excitation source, and is a widely used tool in chemistry and biology. Materials that fluoresce are commonly referred to as phosphors. When light emitted by a phosphor persists for a perceptible duration of time after excitation ceases, i.e., for about 0.1 second or longer, the phenomenon is called phosphorescence.

Recently emerged nanoparticulate fluorescent technology has launched a new era for the development of fluorescent labels using inorganic complexes or particles. These inorganic materials offer substantial advantages over organic dyes, including a longer half-life, a broad excitation spectrum, a narrow, symmetric emission spectrum, and minimal photo-bleaching. Quantum dot technology, however, is still in its infancy, and problems such as the reproducible manufacture, coating, and derivatization of the nanoparticles continue to hinder development. In addition, although the quantum yield of an individual fluorescent nanoparticle is high, the absolute fluorescence intensity of each particle is low. Recent attempts have been made to increase the fluorescence intensity of the particles by grouping multiple particles into a larger single particle; however, such technology is just emerging (Bruchez et al. (1998) Science 281:2013–2016; Chan et al. (1998) Science 281:2016–2018).

Some compounds containing rare-earth elements such as europium (Eu) are known for their unique optical (fluorescent) properties. Fluorescent nanoparticles comprised of europium compounds are disclosed in U.S. Pat. Nos. 6,010,644 and 6,284,156 to Fu et al. Use of these particles to label biological molecules requires expensive and complex chelation chemistry, and therefore, application of such europium chelates has been limited. Also, the particles disclosed by Fu require the presence of boron during manufacture, which may not be desirable in all instances. For example, although the presence of boron allows the reaction temperature to be lowered one or two hundreds degree (° C.), it also results in an increase in the size of the resulting crystals. As fine granularity and small particle size are required in biological applications, particles produced with boron may be unsuitable for biological applications.

Therefore, there remains a need in the art for improved and simplified fluorescent labeling techniques that will provide particles that are suitable for use as labeling agents, and possess high fluorescence intensity. The present invention addresses this need.

SUMMARY OF THE INVENTION

In one embodiment of the invention, a boron-free, europium-containing fluorescent nanoparticle is provided. The nanoparticle is comprised of an aluminum oxide based crystal framework that contains a europium activator; at least one energy reservoir selected from the group consisting of Mg, Ca, Sr, and Ba; and at least one co-activator selected from the group consisting of Sc, Y, La, Ce, Pr, Nd, Sm, Gd, Tb, Dy, Ho, Er, Tm, Yb, Lu, and Bi.

The particle may be surrounded by a coating that contains functional groups and allows for the attachment of the coated particles to chemical and biological molecules. Accordingly, in another embodiment of the invention a boron-free, europium-containing fluorescent nanoparticle is provided that comprises a core comprised of an aluminum oxide base crystal framework; Eu as an activator; at least one energy reservoir selected from the group consisting of Mg, Ca, Sr, and Ba; at least one co-activator selected from the group consisting of Sc, Y, La, Ce, Pr, Nd, Sm, Gd, Tb, Dy, Ho, Er, Tm, Yb, Lu, and Bi; and a coating having functional groups therein.

In another embodiment of the invention, a method for producing such coated, boron-free, europium-containing fluorescent nanoparticles is provided. The method begins by combining aluminum oxide, a europium oxide or salt; at least one salt or oxide of a material selected from the group consisting of Sr, Ca, Mg, and Ba; and at least one co-activator selected from the group consisting of Sc, Y, La, Ce, Pr, Nd, Sm, Gd, Tb, Dy, Ho, Er, Tm, Yb, Lu, and Bi, to form a particulate mixture. The combined materials are then heated under a vacuum to provide the europium-containing fluorescent nanoparticle.

If desired, the method may additionally comprise coating the europium-containing fluorescent nanoparticles with a coating composition having functional groups thereon. The coating is generally a silane and the functional groups are selected from the group consisting of primary amino groups, sulfhydryl groups, aldehyde groups, carboxylate groups, alcohol groups, phosphate groups, ester groups, and ether groups, and combinations thereof. The coating step may be carried out by exposing the europium-containing fluorescent nanoparticle and a coating composition to microwave radiation.

Additional objects, advantages, and novel features of the invention will be set forth in part in the description that follows, and in part will become apparent to those skilled in the art upon examination of the following, or may be learned by practice of the invention.

DETAILED DESCRIPTION OF INVENTION

Figure 1:
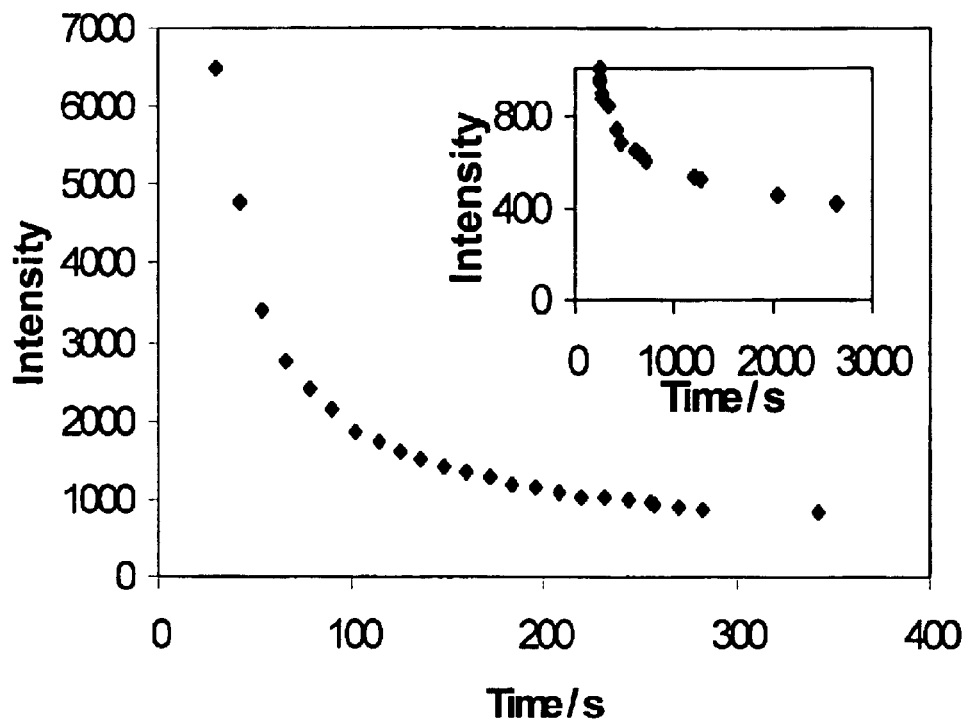
FIG. 1 is a graphical illustration of the emission characteristics of an $EuCaAl_4O_6$ particle.

Definitions:

Before describing the present invention in detail, it is to be understood that unless otherwise indicated this invention is not limited to specific nanoparticle or manufacturing processes, as such may vary. It is also to be understood that the terminology used herein is for the purpose of describing particular embodiments only, and is not intended to be limiting.

It must be noted that, as used herein, the singular forms "a," "an," and "the" include plural referents unless the context clearly dictates otherwise. Thus, for example, "a nanoparticle" encompasses not only a single nanoparticle but also two or more nanoparticles, and the like.

In describing and claiming the present invention, the following terminology will be used in accordance with the definitions set out below.

The term "alkyl" as used herein refers to a branched, unbranched or cyclic saturated hydrocarbon group of 1 to 24 carbon atoms, preferably 1 to 12 carbon atoms, such as methyl, ethyl, n-propyl, isopropyl, n-butyl, isobutyl, t-butyl, octyl, decyl, tetradecyl, hexadecyl, eicosyl, tetracosyl, and the like, as well as cycloalkyl groups such as cyclopentyl, cyclohexyl, and the like. The term "lower alkyl" refers to an alkyl group of 1 to 6 carbon atoms.

The term "aryl" as used herein, and unless otherwise specified, refers to an aromatic moiety containing 1 to 5 aromatic rings. For aryl groups containing more than one aromatic ring, the rings may be fused or linked. Aryl groups are optionally substituted with one or more inert, nonhydrogen substituents per ring; suitable "inert, nonhydrogen" substituents include, for example, halo, haloalkyl (preferably halo-substituted lower alkyl), alkyl (preferably lower alkyl), alkoxy (preferably lower alkoxy), and the like. Unless otherwise indicated, the term "aryl" is also intended to include heteroaromatic moieties, i.e., aromatic heterocycles. Generally, although not necessarily, the heteroatoms will be nitrogen, oxygen, or sulfur.

The term "nanoparticle" refers to a particle, generally a semiconductive or metallic particle, having a diameter in the range of about 1 nm to about 1000 nm, preferably in the range of about 5 nm to about 200 nm, more preferably in the range of about 10 nm to about 100 nm.

The term "emission peak" refers to the wavelength of light that has the highest relative intensity within the characteristic emission spectrum exhibited by semiconductor nanocrystals having a particular size distribution.

The term "excitation wavelength" refers to electromagnetic energy having a shorter wavelength (higher energy) than that of the peak emission wavelength of the semiconductor nanocrystal.

"Silanes" as used herein are compounds that contain one or more silicon-silicon bonds. The term "silanyl" refers to the silane radical. The term "polysilane" is intended to include oligomeric and polymeric silanes, i.e., compounds that include two or more monomeric silane units.

"Silazanes" as used herein are compounds that contain one or more silicon-nitrogen bonds. The term "silazyl" refers to a silazane radical. The term "polysilazane" is intended to include oligomeric and polymeric silazanes, i.e., compounds that include two or more monomeric silazane units.

"Siloxanes" as used herein are compounds that contain one or more silicon-oxygen bonds and may or may not contain cyclic units. The term "siloxyl" refers to a siloxane radical. The terms "polysiloxane" and "siloxane polymer" as used herein are intended to include oligomeric and polymeric siloxanes, i.e., compounds that include two or more monomeric siloxane units.

"Siloxazanes" as used herein are compounds that contain the unit [O—Si—N]. The term "silazanyl" refers to a siloxazane radical. The term "polysiloxazane" is intended to include oligomeric and polymeric siloxazanes, i.e., compounds that include two or more monomeric siloxazane units.

"Carbosilanes" as used herein are compounds that contain one or more silicon-carbon bonds in the backbone and may or may not contain cyclic units. The term "carbosilyl" refers to a carbosilane radical. The terms "polycarbosilane" and "carbosilane polymer" as used herein are intended to include oligomeric and polymeric carbosilanes, i.e., compounds that include two or more monomeric carbosilane units.

The Europium-Containing Fluorescent Nanoparticles:

The boron-free, europium-containing fluorescent nanoparticles of the invention are formed using an aluminum oxide based crystal framework. The aluminum oxide based crystal structure contains europium (Eu) as an activator, as well as at least one energy reservoir selected from the group consisting of Mg, Ca, Sr, and Ba, and at least one co-activator selected from the group consisting of Sc, Y, La, Ce, Pr, Nd, Sm, Gd, Tb, Dy, Ho, Er, Tm, Yb, Lu, and Bi.

The energy reservoir provides for slight modifications in the structure of the aluminum oxide crystal framework, which allows for incorporation of the europium activator and the co-activator. The modified aluminum oxide crystal provides a stored energy source that is capable of maintaining light emission by the particle for approximately 4 to 6 hours after the half intensity time of around 10 minutes.

The color of the light emitted by the nanoparticle may be controlled by the selection of the element(s) used as the energy reservoir. For example, use of calcium as the energy reservoir and its incorporation into the aluminum oxide framework results in the emission of purple light upon excitation with a suitable light source, whereas incorporation of strontium produces a particle that emits green light. The energy reservoir usually constitutes 30 wt. % to approximately 70 wt. % of the nanoparticle. Preferred ranges are between approximately 40 wt. % to approximately 60 wt. %. As noted above, suitable materials for use as the energy reservoir include Mg, Ca, Sr, and Ba. Particularly preferred materials are Sr and Ca.

The aluminum oxide framework will generally represent approximately 30 wt. % to approximately 60 wt. % of the nanoparticle. Preferred fluorescent nanoparticles contain approximately 35 wt. % to approximately 40 wt. % aluminum oxide. Europium typically comprises approximately 0.01 wt. % to approximately 2 wt. % of the nanoparticle, preferably between approximately 0.5 wt. % and 0.8 wt. %.

The co-activator will generally be present in an amount ranging from approximately 0.01 wt. % to approximately 2 wt. %, preferably between approximately 0.5 wt. % and 0.8 wt. % of the nanoparticle. Multiple co-activators may be used, and in a preferred fluorescent nanoparticle at least two co-activators are present. When more than one co-activator is included in the nanoparticle, each co-activator will be present in an amount ranging from approximately 0.01 wt. % to approximately 2 wt. %, preferably between approximately 0.5 wt. % and 0.8 wt. %. Particularly preferred co-activators are La and Nd.

Figure 2:
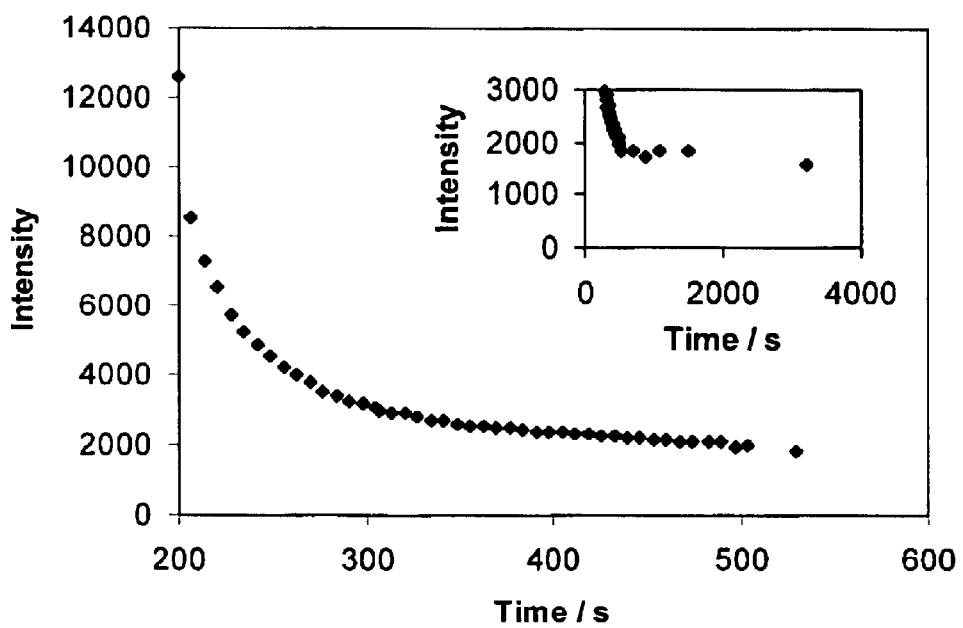
FIG. 2 is a graphical illustration of the emission characteristics of an $EuSrAl_4O_6$ particle.

The nanoparticles of the invention possess unique optical fluorescent properties, and can be designed to emit different wavelengths of light upon excitation. The width of the emission peak displayed by the nanoparticle upon excitation ranges from approximately 40 nm to approximately 80 nm. For example, particles in which calcium is used as the energy reservoir display strong emission at 450 nm when excited, while particles than incorporate strontium give an emission peak at 540 nm. See FIGS. 1 and 2 for a graphical illustration of the emission characteristics of these particles. In particular, FIGS. 1 and 2 are graphs of the intensity of nanoparticle afterglow overtime. For the nanoparticle of the invention, the width of the emission peak at half height is about 50–80 nm, and the half-life time for emission is greater than 200 seconds, which is about a million times longer than that of the fluorescent nanoparticle disclosed by Bruchez Jr. et al., (1998) *Science* 281, 2013–2016. In addition, these particles can be excited by sunlight, UV, or other sources, and no specific light source, such as a laser or other instrument (e.g. fluorometer) is needed.

In one embodiment of the invention, the nanoparticle is coated with a coating composition having one or more functional groups contained thereon. The presence of such a coating allows the nanoparticle to serve as labeling means in chemical and biological applications. The coating is preferably comprised of a silicon-containing compound such as a silane, a siloxane, a silazane, a siloxazane, a carbosilane, or a combination or copolymer thereof. In a preferred embodiment, the silicon-containing compound comprises a functional group through which the nanoparticle may be bound to a small molecule or a biological molecule such as a protein, a nucleic acid, a lipid, or a carbohydrate. Especially preferred functional groups include reactive chemical groups such as, by way of illustration and not limitation, primary amino groups, sulfhydryl groups, aldehyde groups, carboxylate groups, alcohol groups, phosphate groups, ester groups, ether groups, and combinations thereof. Examples of preferred silicon-containing compounds include silanes, especially those comprising a functional group and having the formula:

$$Si(OH)_n(O(CH_2)_pCH_3)_m((CH_2)_qR)$$

where n is an integer from 0–3, m is an integer from 0–3, p is an integer from 0–3, q is an integer from 0–10, and n+m=3; and R is selected from the group consisting of H, halogen, OH, COOH, CHO, $NH_2$, COOR', and OR', where R' is an alkyl or aryl moiety.

The coated nanoparticles may be used as labeling reagents by exploiting the functional groups attached thereto. These groups may be present on the silicon-containing compound at the time of initial reaction of the nanoparticle with the silicon-containing compound, or conveniently may be added at a later time using standard organic synthesis routes by which the reactive group is added to or is substituted for an existing group present on the silicon-containing compound. Methods for adding or substituting reactive chemical groups to silicon-containing compounds such as silane are well-known to those of skill in the art; representative examples of such methods may be found in, e.g., G. T. Hermanson, *Bioconjugate Techniques* (Academic Press, New York, 1996), all the disclosures of which are hereby incorporated by reference.

The nature of the functional group depends, of course, on the chemical nature of the target to be labeled using the nanoparticles of the present invention. In preferred embodiments, the target to be labeled is a biological molecule such as a protein, a nucleic acid, a lipid, or a carbohydrate. For these applications, silane-coated nanoparticles having desirable optical properties, and that are suitable for labeling such a target, may be conveniently prepared by reacting a nanoparticle having a desirable optical property with a silane having a primary amino group, a sulfhydryl group, an aldehyde group, a carboxylate group, an alcohol group, a phosphate group, an ester group, an ether group, or a combinations thereof. Examples of preferred silanes comprising a functional group include $Si(OH)_n(O(CH_2)_pCH_3)_m((CH_2)_qR)$, wherein n is an integer from 0–3, m is an integer from 0–3, p is an integer from 0–3, q is an integer from 0–10, and n+m=3. R is selected from the group consisting of H, halogen, OH, COOH, CHO, $NH_2$, COOR', and OR' where R' is an alkyl or aryl moiety.

Coating the nanoparticles with a silicon-containing compound having one or more functional groups provides an effective way to provide the particle with a group that may be conveniently used to link the particle to a desired target molecule. As one of ordinary skill will readily appreciate, the silane-coated particles may be used to label biological molecules to facilitate analyte detection using any type of assay that currently may be carried out using colored particles such as colloidal gold and latex particles or any other conventionally known fluorescent, chemical, enzymatic, or radiolabeled molecules. These include hybridization assays, FRET assays, enzyme-linked immunosorbent assays ("ELISAs"), latral flow strip assays, competition assays, or any other type of ligand binding assay known to one of skill in the art or developed at a later time that can be adapted for use with the compositions of the present invention.

Nanoparticle Synthesis:

The europium-containing fluorescent nanoparticles of the invention may be prepared by combining: aluminum oxide; a europium oxide or salt; at least one salt or oxide of a material selected from the group consisting of Sr, Ca, Mg, and Ba; and at least one co-activator selected from the group consisting of Sc, Y, La, Ce, Pr, Nd, Sm, Gd, Tb, Dy, Ho, Er, Tm, Yb, Lu, and Bi; to form a particulate mixture. The particulate mixture is then heated under a vacuum to provide the europium-containing fluorescent nanoparticles. Details of these steps are described below.

In addition, the nanoparticles of the invention may be prepared using conventional sintering methods. Such methods begin with the combining and mixing of nano-sized aluminum oxide particles with a solution containing the dissolved salt of the material that is to be used as the energy reservoir. Once the solution containing the dissolved salt of the energy reservoir has been added to the aluminum oxide particles, a second solution containing a dissolved salt or oxide of the europium and any other co-activators that may be desired is added to the aluminum oxide particles. The resulting mixture is then thoroughly ground and mixed. Any remaining solvent is then removed via air-drying or heat evaporation.

The dried mixture is then heated under vacuum to a temperature in the range of approximately 1000° C. to approximately 1600° C. for a period of time ranging from approximately 1 to approximately 5 hours. Preferably, the temperature is increased incrementally over a period of time until the desired temperature is reached and is then incrementally decreased until a temperature of approximately 200° C. is achieved. Suitable temperature ramping rates range from 25° C./hour to approximately 75° C./hour. Such sintering techniques are well known and will be readily understood by those of skill in the art. After sintering is completed, the resulting particles are ground to achieve the desired size. Any conventional grinding or milling procedure, e.g., ball milling, etc., may be used. Generally, particles will range in size from approximately 5 nm in diameter to approximately 200 nm in diameter. Particle sizes ranging from approximately 10 nm to approximately 100 nm in diameter are preferred.

In both conventional methods and the methods of the invention suitable salts include, but are not limited to, halides, nitrates, and carbonates. Any conventional solvent may be used and lower alkyl solvents such as methanol and ethanol are particularly suitable.

If desired, a catalytic amount of a boron salt or oxide can be added to the mixture. However, the methods of the invention can be conducted in the absence of boron. The presence of boron during the sintering process allows for lower temperatures to be used, reducing the reaction temperature approximately 200–400° C. After sintering the resulting particles are suspended and washed in solvent in order to remove the boron catalyst. It is important to note that boron used during the sintering process is not ultimately incorporated into the nanoparticle, as has been confirmed by X-ray diffraction analyses. After the catalyst has been removed, the particles are oven dried and ground as before. As discussed previously, the catalytic use of boron is not preferred as it encourages the formation of excessively large crystals that are unsuitable for many biological applications.

The resulting nanoparticles may then be covered with a coating containing functional groups. The coating is formed, for example, by reaction of the nanoparticles with liquid silanes having a leaving group that is capable of being displaced by any oxygen present in the aluminum oxide framework. Especially preferred leaving groups include $C_{1-4}$ alkoxides or—OH groups. In the coating process, the particles are mixed with a liquid silane, such as 3-aminopropyltrimethoxysilane. The silane/nanoparticle mixture in then subjected to microwave irradiation at a frequency of 2000–2500 MHz for approximately 15 to approximately 20 minutes As will be appreciated by one of skill in the art, the radiation time is subject to change dependent upon microwave power and sample size. The resulting mass is then cooled to room temperature and ground into a fine powder, thereby providing the coated europium-containing fluorescent nanoparticles. The coated nanoparticles may then be used as labeling means as discussed above.

It is to be understood that while the invention has been described in conjunction with the preferred specific embodiments thereof, the foregoing description and the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

EXPERIMENTAL

The following examples are put forth so as to provide those of ordinary skill in the art with a complete disclosure and description of how to prepare and use the compositions disclosed and claimed herein. Efforts have been made to ensure accuracy with respect to numbers (e.g., amounts, temperatures, rates, times, etc.) but some errors and deviations should be accounted for. Unless indicated otherwise, parts are parts by weight, temperature is in degrees Celsius (° C.), and pressure is at or near atmospheric. Additionally, all starting materials were obtained commercially or synthesized using known procedures.

Example 1

Europium-Containing Fluorescent Nanoparticle Formation 5.14 g of $Al_2O_3$, was placed in a porcelain mortar. 7.18 g of $Sr_2CO_3$ salt was dissolved in ethanol and added to the $Al_2O_3$ powder. Then 0.089 g of $Eu_2O_3$, 0.084 g of $La_2O_3$, and 0.081 g of $Nd_2O_3$ were suspended in ethanol and added to the $Al_2O_3$ powder. The mixture was then blended and ground thoroughly with a porcelain pestle. After air or heat evaporation of ethanol, the dried particle mixture was placed in an environment of argon gas containing 1–2% hydrogen. Under a vacuum, the mixture was gradually heated at a rate of 50° C./hour until the temperature was 400° C. where it was held for 10 min. Then the temperature was raised to 800° C. Where it was held for 20 min, then to 1200° C. and held for 40 min, and then the temperature was increased to 1400° C., and allowed to remain at 1400° C. for 2–4 hours. The temperature was decreased to 200° C. at a rate of 50° C./hour and then the mixture was allowed to sit overnight.

Example 2

Europium-Containing Fluorescent Nanoparticle Formation

The nanoparticles were prepared as described in Example 1, however, 0.25 g of $H_3BO_3$ was added to the mixture in order to decrease the reaction temperature. Using $H_3BO_3$ can decrease the reaction temperature 200–400° C. In this method, the mixture was heated to 1200° C. The resulting particles were suspended in ethanol after cooling and then washed with ethanol three times in order to remove the $H_3BO_3$. X-ray diffraction analysis of the particles clearly indicates that boron, either in elemental form, as an oxide, or as an acid is not present in the final particle.

Example 3

Figure 3:
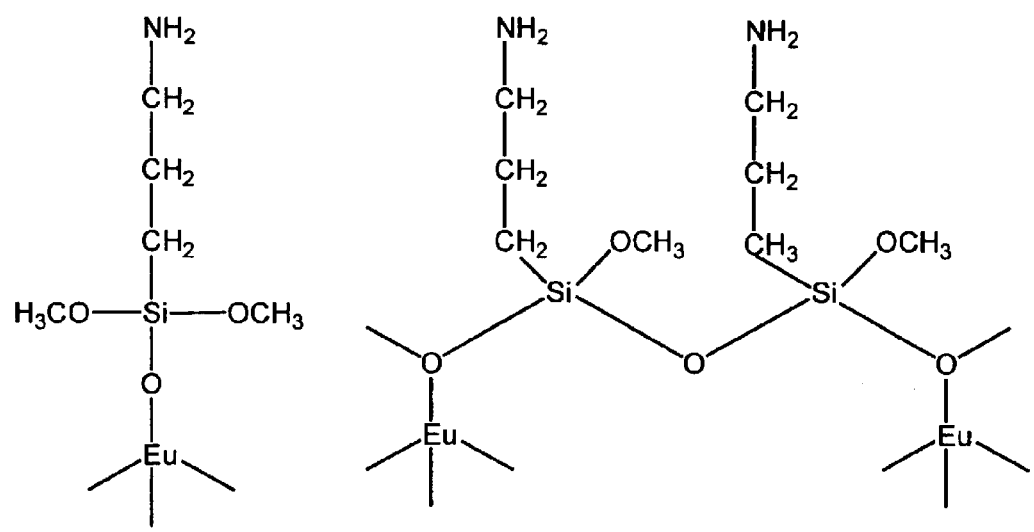
FIG. 3 depicts the bonding chemistry for attachment of a silane coating to the surface of a fluorescent nanoparticle of the invention.

Coating Europium-Containing Fluorescent Nanoparticles 2 g of the particles prepared in Example 1 were placed in a container such as a round-bottom flask or beaker. The particles were oven dried at 100–105° C. for 2–4 hours. Then, 3–4 mL of 3-aminopropyltrimethoxysilane coating reagent was added until the particles were completely covered. The mixture was then mixed with a magnetic stir bar or gently rotated in a vapor rotor at room temperature for 24 hours and at 80–100° C. for 12 hours. The particles were separated by centrifugation at 10,000 g for 5–10 min and the excess coating reagent removed by pipette. The resulting pellet of particles was heated in a microwave oven for 15–20 min (a brief break may be needed during microwave heating with a 3–5 min interval) until the particles dried. After drying, the coated particles were placed in a porcelain mortar and a small amount of ethanol was added and mixed. The particles were then ground with a porcelain pestle and allowed to air dry. FIG. 3 depicts the bonding chemistry for the attachment of the silane coating to the surface of the fluorescent nanoparticle.

Example 4

Figure 4:
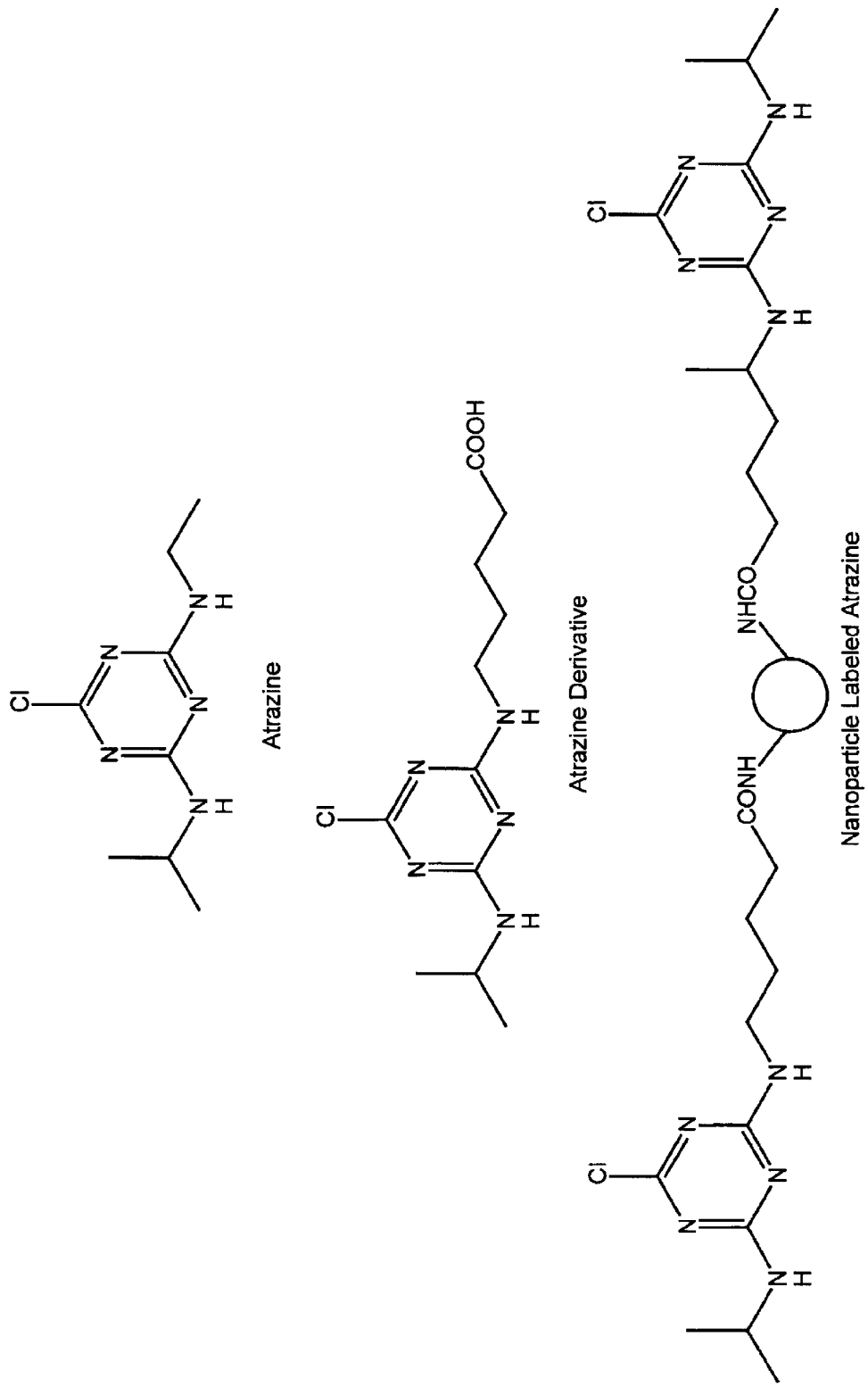
FIG. 4 depicts the reaction chemistry for the attachment of atrazine to 3-aminopropyltrimethyxysilane coated europium-containing fluorescent nanoparticles, as described in Example 4.

Use of Coated Europium-Containing Fluorescent Nanoparticles in Small Molecule Herbicide Atrazine Detection The coated particles prepared in Example 3 were used as labels for an immunoassay to detect the herbicide atrazine. After being coated with 3-aminopropyltrimethoxysilane, the particles were conjugated and labeled onto an atrazine analog (FIG. 4). The labeled atrazine was incubated with free atrazine and anti-atrazine antibodies in a competitive format. With a separation step using magnetic beads, fluorescent intensity in antibody-phase or aqueous-phase was measured by fluorospectrometer. The increase of fluorescence in antibody-phase (or decrease of fluorescence in aqueous-phase) is proportional to the concentration of atrazine in the sample. This format could detect low pM levels of atrazine in the sample, which demonstrates that these inorganic fluorescent particles with a simple coating treatment can be used as a unique fluorescent label in biological sciences. This assay using the inorganic fluorescent particles is much more sensitive than an enzyme linked immunosorbent assay optimized with the same antibody and hapten.

Example 5

Use of Coated Europium-Containing Fluorescent Nanoparticles in the Detection of Ubiquitin The coated particles prepared in Example 3 were used as labels for the detection of peptide ubiquitin. The 3-aminopropyltrimethoxysilane coated particles were conjugated with ubiquitin (U6253, Sigma Chem. Co) using carbodiimide. Ubiquitin (10 mg) was dissolved in 1 mL 0.1 M sodium phosphate (pH 7.3), and 1 mL of coated particle suspension (containing 20 mg particles) was added with stirring. To this solution, 6.5 mg of conjugate reagent EDC (1-ethyl-3-(3-dimethylaminopropyl) carbodiimide hydrochloride) was then added and allowed to react for 2 hours at room temperature. The conjugate was separated out by centrifugation at 14,000 rpm for 10 min. The ubiquitin was then detected using methods similar to those described in Example 3. The labeled ubiquitin was incubated with free ubiquitin and anti-ubiquitin antibodies (U 5379, Sigma Chem Co) in a competitive format. The sensitivity for ubiquitin is as low as 0.5 nM in this system.

Example 6

Use of Coated Europium-Containing Fluorescent Nanoparticles in the Detection of Soy Protein The coated particles prepared in Example 3 were used as labels for the detection of soy protein in a lateral flow strip system. The 3-aminopropyltrimethoxysilane coated nanoparticles were conjugated with anti-soy protein polyclonal antibody (S2519, Sigma Chem. Co) using carbodiimide method described in Experiment 5. Labeled antibody was loaded onto the portion of the strip located above the sample contact area. In the upper level of strip (about 1/16 inch width signal region), antibodies were immobilized (by spraying on to nitrocellular membrane). For assaying, the reaction portion of the strip was placed into a sample solution containing the target soy protein. The assay buffer carrying soy protein moved towards labeled antibody region. Soy proteins present in the sample solution bonded with labeled antibodies and continued to move upwards until reaching the signal region where they remained. Excited by a UV light for 30 seconds, the positive signal band was clearly visible in a darkened environment. The resulting system displays far more sensitivity than the conventionally used colloidal gold-labeled strip assay.

We claim:

1. A boron-free, europium-containing fluorescent nanoparticle comprising an aluminum oxide base crystal framework; Eu as an activator; at least one energy reservoir selected from the group consisting of Mg, Ca, Sr, and Ba; and at least one co-activator selected from the group consisting of Sc, Y, La, Ce, Pr, Nd, Sm, Gd, Tb, Dy, Ho, Er, Tm, Yb, Lu, and Bi, wherein the width of the emission peak displayed by the nanoparticle upon excitation ranges from approximately 40 nm to approximately 80 nm.

2. The nanoparticle of claim 1, wherein the co-activator is selected from the group consisting of La and Nd.

3. The nanoparticle of claim 1, wherein the nanoparticle has a diameter ranging from approximately 5 nm to approximately 200 nm.

4. The nanoparticle of claim 1, wherein the nanoparticle further comprises a coating having functional groups therein.

5. The nanoparticle of claim 4, wherein the functional groups are selected from the group consisting of primary amino groups, sulfhydryl groups, aldehyde groups, carboxylate groups, alcohol groups, phosphate groups, ester groups, and ether groups, and combinations thereof.

6. The nanoparticle of claim 4, wherein the coating is comprised of a silicon-containing compound.

7. The nanoparticle of claim 6, wherein the silicon-containing compound has the structural formula $$Si(OH)_n(O(CH_2)_pCH_3)_m((CH_2)_qR)$$

wherein n is an integer from 0–3, m is an integer from 0–3, p is an integer from 0–3, q is an integer from 0–10, and n+m=3; and R is selected from the group consisting of H, halogen, OH, COOH, CHO, NH$_2$, COOR', and OR' where R' is an alkyl or aryl moiety.

8. The nanoparticle of claim 1, which comprises at least two co-activators.

9. The nanoparticle of claim 1, wherein the half-life for emission upon excitation is greater than approximately 200 seconds.

10. A method for preparing a europium-containing fluorescent nanoparticle comprising the steps of:
   (a) combining:
      (i) aluminum oxide;
      (ii) a europium oxide or salt;
      (iii) at least one salt or oxide of a material selected from the group consisting of Sr, Ca, Mg, and Ba; and
      (iv) at least one co-activator selected from the group consisting of Sc, Y, La, Ce, Pr, Nd, Sm, Gd, Tb, Dy, Ho, Er, Tm, Yb, Lu, and Bi;
   to form a particulate mixture; and
   (b) heating the particulate mixture under a vacuum to provide the europium-containing fluorescent nanoparticle.

11. The method of claim 10, wherein the salt is selected from the group consisting of nitrates, carbonates and halides.

12. The method of claim 10, wherein the co-activator is selected from the group consisting of La and Nd.

13. The method of claim 10, further comprising after step (b), step (c) coating the europium-containing fluorescent nanoparticle with a coating composition having one or more functional groups thereon.

14. The method of claim 13, wherein the functional groups are selected from the group consisting of primary amino groups, sulfhydryl groups, aldehyde groups, carboxylate groups, alcohol groups, phosphate groups, ester groups, and ether groups, and combinations thereof.

15. The method of claim 13, wherein the coating composition is comprised of a silicon-containing compound.

16. The method of claim 15, wherein the silicon-containing compound has the structural formula $$Si(OH)_n(O(CH_2)_pCH_3)_m((CH_2)_qR)$$

wherein n is an integer from 0–3, m is an integer from 0–3, p is an integer from 0–3, q is an integer from 0–10, and n+m=3; and R is selected from the group consisting of H, halogen, OH, COOH, CHO, NH$_2$, COOR', and OR' where R' is an alkyl or aryl moiety.

17. The method of claim 13, wherein the coating step comprises exposing the europium-containing fluorescent nanoparticle and the coating composition to microwave radiation.

* * * * *